United States Patent [19]

Fox

[11] Patent Number: 4,722,331

[45] Date of Patent: Feb. 2, 1988

[54] ORTHOPAEDIC TOOL GUIDE

[76] Inventor: James M. Fox, 5429 Louise Ave., Encino, Calif. 91316

[21] Appl. No.: 772,168

[22] Filed: Sep. 3, 1985

[51] Int. Cl.[4] .............................................. A61F 5/04
[52] U.S. Cl. .............................................. 128/92 VD
[58] Field of Search ................... 128/305, 305.1, 310, 128/92 XV, 92 VY, 92 XX; 408/72 R; 83/427

[56] References Cited

U.S. PATENT DOCUMENTS

| 268,614 | 12/1882 | Brown | 433/72 |
|---|---|---|---|
| 596,375 | 12/1897 | Murchie . | |
| 2,697,433 | 12/1945 | Zehnder | 128/83 |
| 3,135,263 | 6/1964 | Connelly, Jr. | 128/310 |
| 3,704,707 | 12/1972 | Halloran | 128/92 EB |
| 4,159,716 | 7/1979 | Borchers | 128/80 R |
| 4,257,411 | 3/1981 | Cho | 128/92 XV |
| 4,335,715 | 6/1982 | Kirkley | 128/92 EB |
| 4,340,059 | 7/1982 | Marinoff | 128/305 |
| 4,450,834 | 5/1984 | Fischer | 128/92 EB |
| 4,535,768 | 8/1985 | Hourahane et al. | 128/92 EB |

FOREIGN PATENT DOCUMENTS

| 910078 | 1/1946 | France | 19/1 |
|---|---|---|---|
| 515814 | 2/1955 | Italy | 128/92 XV |
| 92611 | 2/1953 | Sweden . | |

OTHER PUBLICATIONS

Verne et al., "Etude critique des methodes de visee pour l'enclouage extra-articulaire des fractures cervicales vraies du femur," pp. 196-223 (French).

"Instrument for Pegging Fractures of the Neck of the Femur," *Instrument Makar's Bow and Arrow* (literature).

Hustinx, "Instrument Zur Nagelung von Schenkelhalsbruchen," *Zentralblatt Fur Chirurgie*, 1937, pp. 2316-2320; with translation.

"Arthroscopic Ligament Drill Guide," *Richards Medical Company*, literature.

"Repair or Reconstruction of the Cruciate Anterior Ligament with the Stille Drill Guide." DePuy, 1979, (literature).

"Simple" and Combined Aiming Devices, *Synthes* (Commercial literature).

*Primary Examiner*—Richard J. Apley
*Assistant Examiner*—David Isabella

[57] ABSTRACT

An orthopaedic tool guide apparatus, including a tool member, a probe and, extending therebetween, a connecting structure, is arranged to enable adjustment of the positional relationship of the tool member to the probe over a range of positions in which the axis of the tool member remains aligned with the end of the probe. The connecting structure includes first and second arms hinged together at respective ends, the tool member connected to the first the arm and the probe being connected to the second the arm at positions spaced from the axis of the hinge, whereby one of the arms can be rotated relative to the other the arm through a series of different planes to enable the apparatus to be manuvered relative to the body. The axes of the hinge and the tool member are arranged to intersect at a predetermined target point, and the end of the probe is disposed at the target point.

9 Claims, 4 Drawing Figures

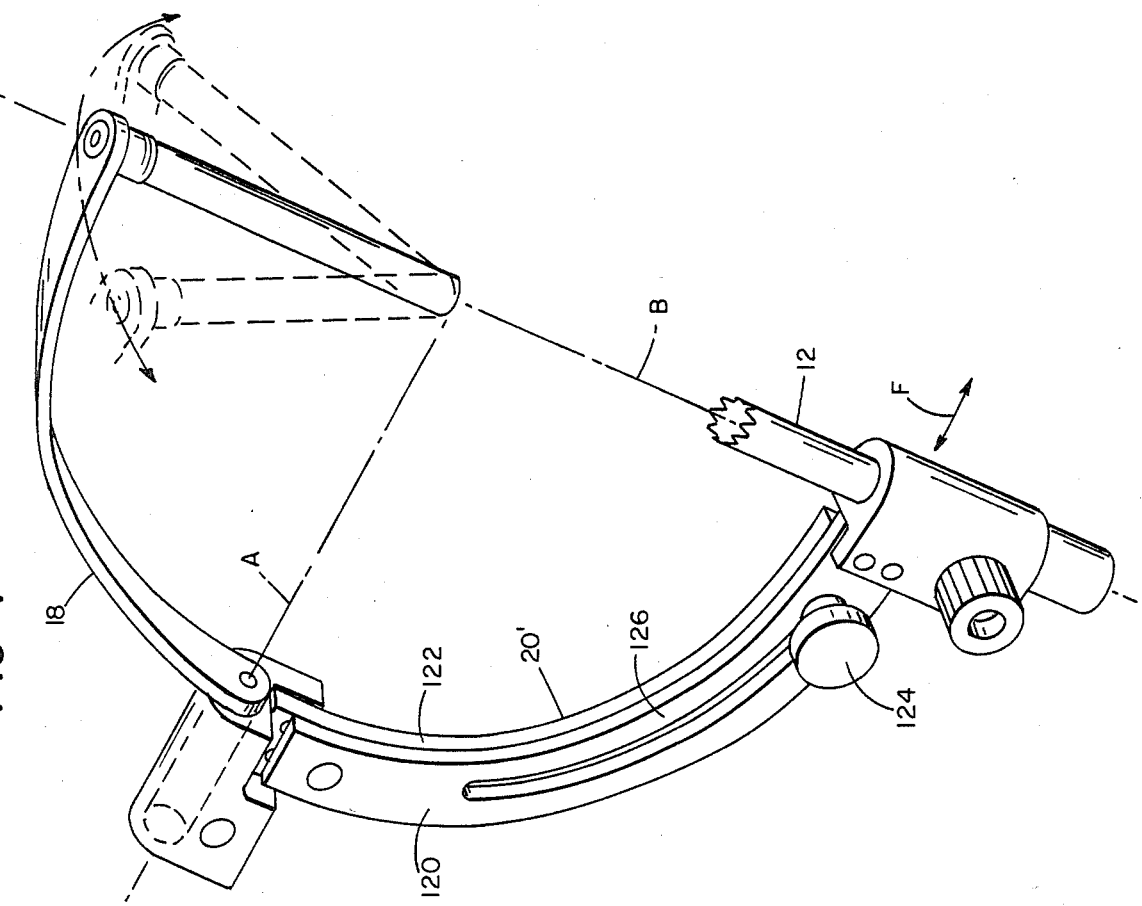
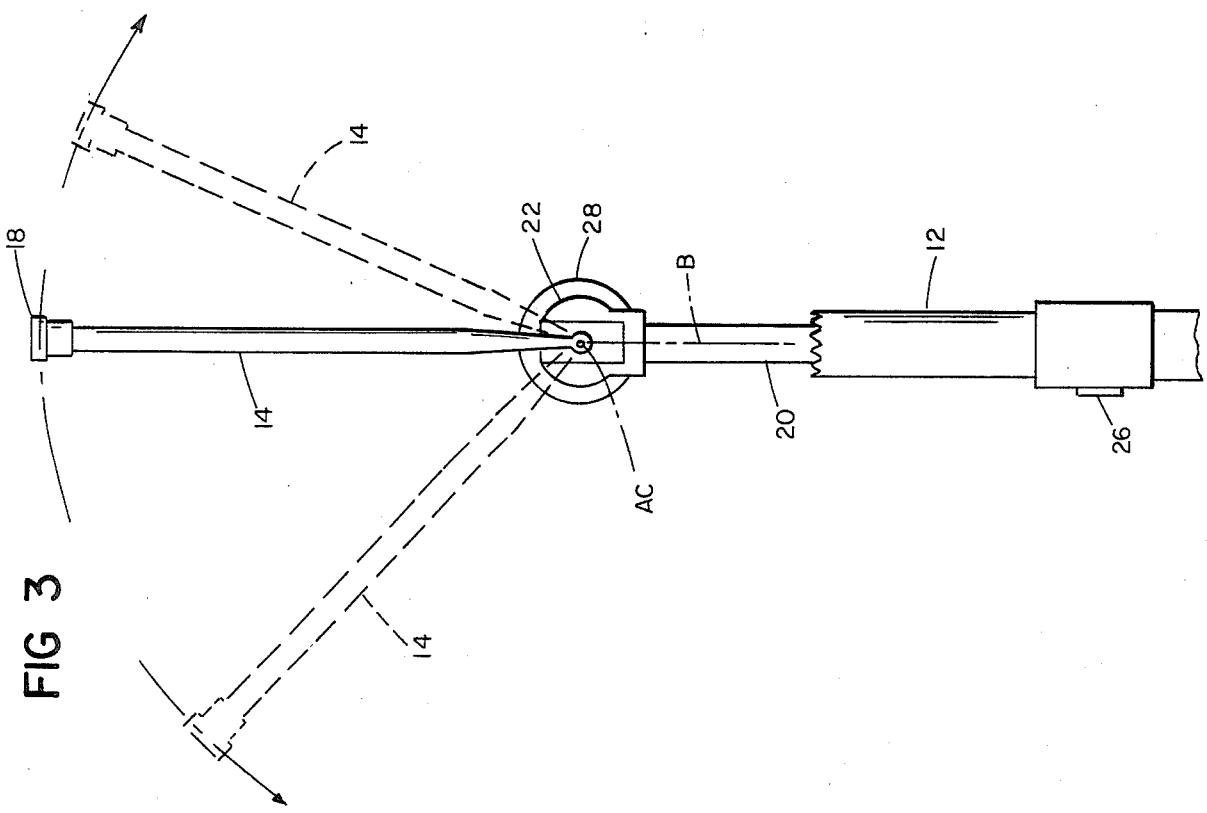

ORTHOPAEDIC TOOL GUIDE

BACKGROUND OF THE INVENTION

The invention relates to tool positioning devices for use by orthopaedists.

In some orthopaedic operations, e.g., reconstruction of the anterior and/or posterior cruciate ligaments, repair of acute ligamentous injuries, subchondral drilling, and fixation of chondral fractures, holes are drilled into or through bone, e.g., in the knee. The angle and position of the hole is critical to the surgeon, and the tool guide provides means to determine in advance the angle the drill will follow through the bone, and the precise point at which the tip will emerge from the bone. Tool guides of this type typically include a target, which is positioned adjacent the point at which it is desired to have the drill tip emerge, a drill or other tool member having an axis aligned with the target, and intervening supporting structure. The relative positions of the drill and the target are usually adjustable to a limited degree (in a plane) in a manner to maintain the alignment of the drill with the target.

Objectives of this invention include providing a tool guide that can be used with great facility; providing a tool guide useful over a wide range of possible approaches to the operative site; and a tool guide that can be employed extensively in arthoscopic surgery.

SUMMARY

In general, the invention concerns an orthopaedic tool guide apparatus comprising a tool member, a probe and, extending therebetween, a connecting structure, the apparatus arranged to enable adjustment of the positional relationship of the tool member to the probe over a range of positions in which the axis of the tool member remains aligned with the end of the probe.

According to the invention, the connecting structure comprises first and second arms hinged together at respective ends, the tool member connected to the first arm and the probe being connected to the second arm at positions spaced from the axis of the hinge, the axes of the hinge and the tool member being arranged to intersect at a predetermined target point, and the end of the probe being disposed at the target point, whereby one of the arms can be rotated relative to the other arm through a series of different planes to enable the apparatus to be manuvered relative to the body.

In preferred embodiments, one arm is curved with a first radius generally corresponding to the distance between the probe end and the hinge, and another the arm is curved with a second radius greater than the first radius to permit clearance between the arms during rotation; the probe is a generally straight member extending radially with respect to a sphere centered on the target point; the probe is constructed and arranged for introduction into a joint of a body via a puncture opening, preferrably the probe is approximately 6 inches in length and the apparatus is adapted for use about the knee; the arm connected to the tool member is adapted for use as a handle; the tool member is adapted to fixedly engage the surface to be drilled, preferably the tool member has a serrated distal end; the arms are of unequal length; and the tool member may be moved along the respective arm.

Other features and advantages of the invention will be understood from the following description of the presently preferred embodiment, and from the claims.

PREFERRED EMBODIMENT

We first briefly describe the drawings.

Drawings

FIG. 3 is a plan view of the tool guide, illustrating positions of adjustment; and FIG. 4 is a perspective view of another embodiment of the invention.

Figure 1:
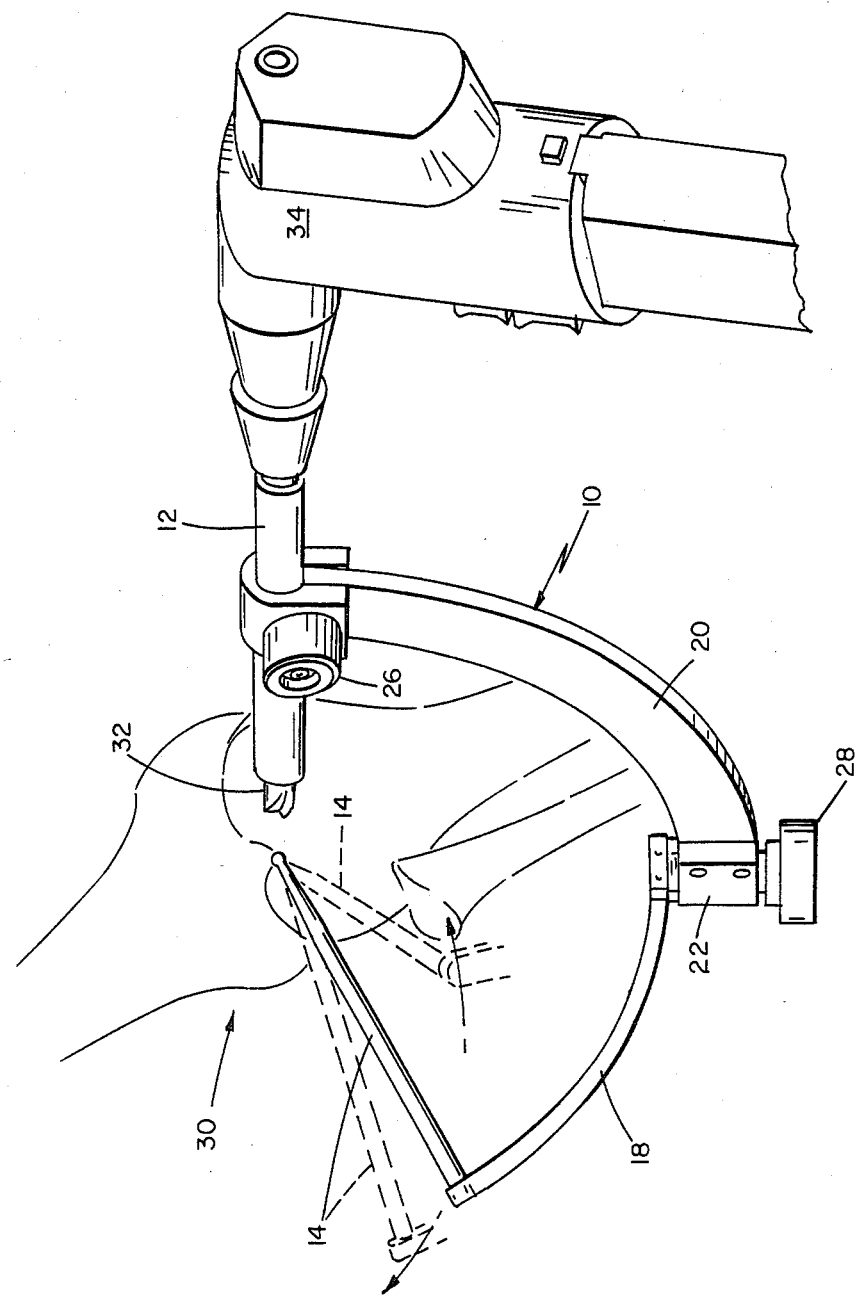
FIG. 1 is a perspective view of the orthopaedic tool guide apparatus of the invention, positioned about the knee.
Figure 2:
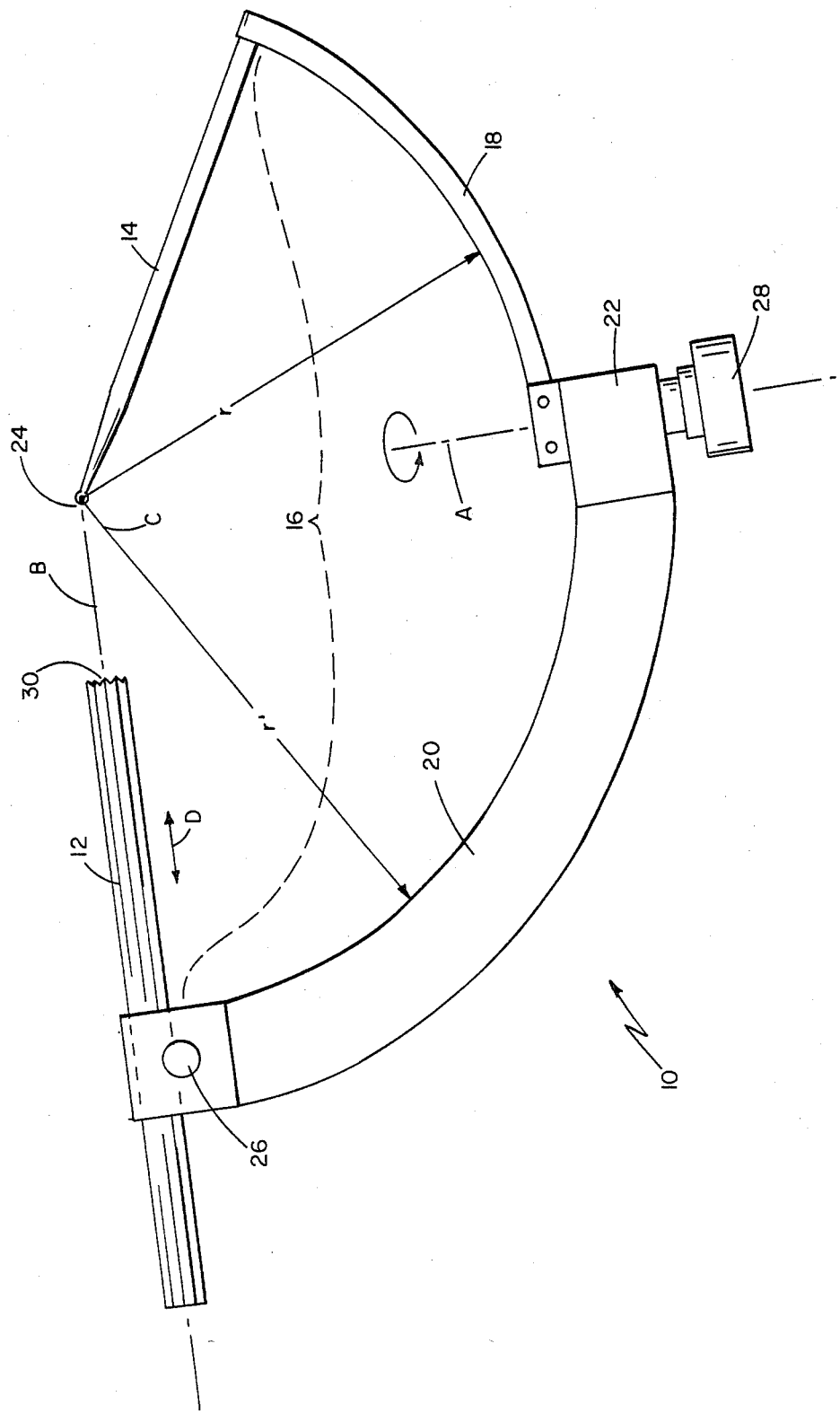
FIG. 2 is a side view of the tool guide.

Referring to FIGS. 1 and 2, the tool guide apparatus 10 of the invention consists of a tool member 12, a probe 14 and, extending therebetween, a connecting structure 16, all typically formed of stainless steel. The connecting structure consists of a pair of arcuate arms 18, 20 extending from hinge 22 and respectively supporting the tool member and the probe at positions spaced from the hinge. The axis, A, of the hinge and the axis, B, of the tool member are arranged to intersect at the target point, C, where the free end 24 of the probe is diposed.

The arms are adapted for rotation about hinge axis, A, through a series of different planes to enable the apparatus to be manuvered relative to the body, by changing the spacial relationship of tool member 12 and probe 14. This is shown in FIGS. 1, 3 and 4 by the dashed line representations on the probe showing it in several positions of rotation about hinge axis A, relative to tool member support arm 20. Once positioned, the arms are fixed by means of knob 28.

Thus the device of the invention overcomes a difficulty experienced with the numerous ligament drill guide positioning devices available on the market, i.e., the lack of mobility after the intra-articular point has been reached with the probe tip and the surgeon is unable, because of the bony anatomy, to maneuver the tool member portion of the apparatus to the desired extra-articular position for drilling. The tool guide apparatus of the invention allows the surgeon mobility after choosing his target point and reaching his chosen extra-articular position, allows the surgeon versatility in choosing his extra-articular point, and allows the surgeon to feel confident of reaching the intra-articular space so desired.

Probe-supporting arm 18 is curved with a radius, r, corresponding to the distance between the hinge axis and the base of the probe, about three inches (7.5 cms) for use in the adult knee. The tool member-supporting arm 20 is curved with a radius, r', greater than radius, r, to permit clearance between the arms during rotation. The longer, tool-member-supporting arm 20 is also relatively more rugged to allow use as a handle, e.g., during drilling.

Tool member 12 consists of a hollow tube on axis, B, sized and adpated to permit drilling through the tube, along its axis. The radial position of the tool member along axis, B, relative to arm 20, is fixed during drilling, but adjustment along the axis, indicated by arrow, D in FIG. 2, is achieved by loosening screw 26. The inner end of the tool member has serrations 30 for more secure engagement with the surface to be drilled.

Probe 14 is sized and adapted for insertion via a puncture into a joint, e.g., the knee, as shown in FIG. 1, with the surgeon positioning the probe tip by viewing through an arthroscope. The tip of the probe is also serrated to enhance viewability via the arthroscope.

The tool guide apparatus 10 of the invention is useful generally in orthopaedic procedures for drilling in bone toward a remote point. By way of example, with reference generally to FIG. 2, to provide a tibial hole for fixation of the anterior cruciate ligament in the knee 30, the following procedure may be employed:

A. The specific position desired by the surgeon for the tibial origin is visualized, either by arthroscopy or arthrotomy.

B. The probe 14 is inserted from a medial or lateral side approach. (If the surgical procedure is performed arthroscopically, the probe inserted via a puncture opening through the flesh.)

C. The tool member support arm 20 and the probe support arm 18 are adjusted through the radii of a sphere about a center at the target point, C, including by rotation of the arms about the hinge axis, A, to place the end of the tool member at a point approximately three to five centimeters below the level of the tibial plateau. (If the probe is inserted percutaneously, its range of adjustment is somewhat limited, but rotation of the axis about hinge axis, A, provides sufficient flexibility for the surgeon to obtain the desired placement.)

D. The locking mechanism 28 is tightened to maintain the fixed radius position and the guide 10 is held in position while a distal skin incision made.

E. The serrated tool member 12 is extended to the tibial periosteal surface and is tightened utilizing the locking mechanism 26.

F. A drill bit 32 on powered drill 34 is inserted through tool member 12 and a hole drilled into the tibia bone 36.

G. Sequential diameter drill bits are used to enlarge this hole accordingly to the selected diameter.

OTHER EMBODIMENTS

Other embodiments are within the following claims. For example, the dimensions mentioned above are given only by way of example. The apparatus may be used in other areas of the body, including joints of the body other than the knee, both percutaneously and in conjunction with open surgery, and other dimensions may be specified. The probe and probe tip may have configurations other than those described. Also, the position of the probe or the tool member relative to the hinge may be adjustable. For example, referring to FIG. 4, the tool-member-support arm 20' consists of two, overlying arm elements 120, 122, which permits extension of the underlying arm 122 along a curve projected along arm 120, indicated by arrow, F, for adjustment of the position of the tool member relative to the hinge. Screw 124 postioned in slot 126 may be tightened to fix the arm elements at the desired position.

What is claimed is:

1. An orthopaedic tool guide apparatus for orthopaedic surgery of boney tissue of a living body comprising:
a tool member disposed upon a first axis aligned with a target point,
a probe having a free end disposed at said target point, said probe disposed upon a second axis aligned to intersect said first axis at said target point, and
connecting structure supporting said tool member and said probe in alignment with said first and second axes, said connecting structure adapted to maintain said tool member and said probe in aligned relationship, with the free end of said probe at said target point, during adjustment of the positional relationship of said probe and said tool member over a range of positions, the free end of the probe adapted to be positioned for surgery at a said target point in the living body and said tool member adapted to be positioned in alignment therewith, with boney tissue of the living body disposed therebetween,
said connecting structure comprising a first arm and a second arm, said arms hinged together at respective first ends of each said arm on a third axis in intersection with said target point, each said arm extending in cantilever fashion from said hinge, said tool member supported by said first arm at a position spaced from said third axis and said probe supported by said second arm at a position spaced from said third axis, said first arm and said second arm, with the free end of said probe disposed at said target point in the body, adapted for relative rotation about said third axis through non-coincident planes intersecting said third axis for positioning of said tool member with said first axis passing through a desired region of intervening boney tissue.

2. The tool guide apparatus of claim 1 wherein said second arm is curved with a first radius generally corresponding to the distance between the free end of said probe and said hinge, and said second arm is curved with a second radius greater than said first radius to permit clearance between the arms during relative rotation about said third axis.

3. The tool guide apparatus of claim 1 wherein said probe is a generally straight member disposed along said second axis.

4. The tool guide apparatus of claim 1 wherein the free end of said probe is sized and constructed for introduction via a puncture opening into a joint space of a living body.

5. The tool guide apparatus of claim 4 wherein said probe is approximately 6 inches in length, and said apparatus is sized and constructed for surgery of the knee.

6. The tool guide apparatus of claim 1 wherein said tool member comprises means for fixed engagement of said tool member to an intervening surface along said first axis, between said target point and said tool member.

7. The tool guide apparatus of claim 6 wherein said means for fixed engagement of said tool member comprises a serrated distal end.

8. The tool guide apparatus of claim 1 wherein said arms are of unequal length.

9. The tool guide apparatus of claim 1 wherein said tool member further comprises means for releasable attachment of said tool member to said first arm whereby the position of said tool member along said first arm is adjustable.

* * * * *